United States Patent [19]

Yamamoto et al.

[11] Patent Number: 5,312,989
[45] Date of Patent: May 17, 1994

[54] METHOD FOR THE PURIFICATION OF 4,4'-DIAMINO-DIPHENYLMETHANE

[75] Inventors: Takahiro Yamamoto, Oita; Hirokazu Murata, Osaka; Kiichi Hattori, Oita, all of Japan

[73] Assignee: Sumitomo Chemical Co., Ltd., Osaka, Japan

[21] Appl. No.: 68,229

[22] Filed: May 28, 1993

[30] Foreign Application Priority Data

May 29, 1992 [JP] Japan .................................. 4-138673

[51] Int. Cl.$^5$ ............................................ C07C 209/84
[52] U.S. Cl. ..................................................... 564/334
[58] Field of Search .......................................... 564/334

[56] References Cited

FOREIGN PATENT DOCUMENTS 745173 10/1966 Canada .
1169127 10/1969 United Kingdom .

Primary Examiner—Richard L. Raymond
Attorney, Agent, or Firm—Birch, Stewart, Kolasch & Birch

[57] ABSTRACT

A method of purifying 4,4'-diaminodiphenylmethane comprising partially melting a crystal of crude 4,4'-diaminodiphenylmethane and removing a melt to obtain a high purity 4,4'-diaminodiphenylmethane. By utilizing the method, a high purity 4,4'-diaminodiphenylmethane is obtained efficiently with a low level of energy consumption.

13 Claims, No Drawings

METHOD FOR THE PURIFICATION OF 4,4'-DIAMINO-DIPHENYLMETHANE

BACKGROUND OF THE INVENTION

1. Field of the Invention

The present invention relates to a method of purifying 4,4'-diaminodiphenylmethane, which is useful as an intermediate in the preparation of polyurethane or as an additive for rubbers.

2. Description of the Related Art 4,4'-Diaminodiphenylmethane can be prepared by reacting aniline and formaldehyde. But, in addition to the desired 4,4'-diaminodiphenylmethane, many by-products such as polymeric condensates (e.g. polymethylenepolyphenylamine) and diaminodiphenylmethane isomers (e.g. 4,2'-diaminodiphenylmethane and 2,2'-diaminodiphenylmethane) are produced. Therefore, further purification of 4,4'-diaminodiphenylmethane is necessary to improve its quality.

However, using conventional rectification, cause a part of the 4,4'-diaminodiphenylmethane to be lost because of thermal deterioration, or the separation of by-products having close boiling points to that of 4,4'-diaminodiphenylmethane (such as diaminodiphenylmethane isomers) is difficult. Moreover, in an industrial scale production, rectification is not advantageous in view of energy consumption, and facilities and equipment requirements.

It has been proposed to purify 4,4'-diaminodiphenylmethane by forming an adduct of 4,4'-diaminodiphenylmethane with an alkali metal halide or cyanide, separating the adduct and decomposing the adduct to recover 4,4'-diaminodiphenylmethane (GB Patent No. 1 169 127), or by condensation reacting aniline and formaldehyde, and diluting, partially neutralizing, crystallizing and neutralizing the product (Canadian Patent No. 745,173). However, these methods are troublesome or insufficient in purification effects, or provide low productivity for the desired product per unit volume. Therefore, these methods are unsatisfactory for the industrial production of 4,4'-diaminodiphenylmethane.

SUMMARY OF THE PRESENT INVENTION

An object of the present invention is to provide a method for the purification of 4,4'-diaminodiphenylmethane which is less troublesome than the conventional purification methods, and which can be industrially used.

According to the present invention, there is provided a method for the purification of 4,4'-diaminodiphenylmethane, the method comprising partially melting a crystal of crude 4,4'-diaminodiphenylmethane and removing a melt to obtain a high purity 4,4'-diaminodiphenylmethane.

DETAILED DESCRIPTION OF THE INVENTION

In the present invention, crude 4,4'-diaminodiphenylmethane may be obtained by removing unreacted starting materials or high boiling products from a reaction mixture prepared through the reaction of aniline and formaldehyde by, for example, recrystallization or simple distillation under reduced pressure. Preferably, crude 4,4'-diaminodiphenylmethane contains at least 90% by weight of 4,4'-diaminodiphenylmethane and 10% by weight or less of impurities such as diaminodiphenylmethane isomers (e.g. 4,2'-diaminodiphenylmethane or 2,2'-diaminodiphenylmethane), polymethylenepolyphenylamines (e.g. $\alpha,\alpha'$-di(4-aminophenyl)xylidine).

Although polymers such as polymethylenepolyphenylamine are impurities having the boiling points higher than that of 4,4'-diaminodiphenylmethane, they can be removed by the purification method of the present invention.

For carrying out the purification method of the present invention, any apparatus that can control its internal temperature and separate a melt from a crystal, for example, a reactor having a valve at its bottom, or a crystallizer may be used.

The crystal of crude 4,4'-diaminodiphenylmethane may be of any form, for example, bulk, particle or powder.

A temperature at which the crystal of crude 4,4'-diaminodiphenylmethane is partially molten is usually from 70° to 93° C. In general, the crude 4,4'-diaminodiphenylmethane is slowly heated. In particular, in a temperature range higher than 70° C., it is heated at a heating rate of 6° C./hour or less, preferably 2° C./hour or less, more preferably 1° C./hour or less.

If necessary, a small amount of a solvent may be added. Examples of the solvent are aniline, benzene, toluene, chlorobenzene and the like.

The amount of the melt depends on the purity of crude 4,4'-diaminodiphenylmethane, the required purity of purified 4,4'-diaminodiphenylmethane, purification conditions, and so on. The amount of the melt is usually from 20 to 90% by weight, preferably from 50 to 80% by weight, more preferably from 60 to 80% by weight based on the weight of charged crystals of crude 4,4'-diaminodiphenylmethane.

The melt can be removed through the bottom valve of the reactor, or the like. The melt can be removed successively or at one time. Preferably the melt is successively removed. The removed melt can be recycled.

The purity of purified 4,4'-diaminodiphenylmethane can vary according to the final use of 4,4'-diaminodiphenylmethane or the purification conditions. Usually, the purity of 4,4'-diaminodiphenylmethane is at least 97%.

The purified 4,4'-diaminodiphenylmethane can be recovered by a conventional method, for example, by cooling and removing crystallized 4,4'-diaminodiphenylmethane from the apparatus, or by melting 4,4'-diaminodiphenylmethane once and removing molten 4,4'-diaminodiphenylmethane from the apparatus.

In the present invention, when the crude 4,4'-diaminodiphenylmethane crystal is once liquefied by melting and recrystallized by gradual cooling, the purification effect is further increased. If necessary, a small amount of a solvent such as an aromatic amine, aromatic hydrocarbon or aromatic halohydrocarbon (e.g. aniline, benzene, toluene, chlorobenzene, etc.) may be added.

The liquefied crude 4,4'-diaminodiphenylmethane is gradually cooled to 60° C., preferably at a cooling rate of 5° C./hour or less, more preferably 1° C./hour or less to crystallize it.

The cooling temperature is usually 60° C. or lower, preferably 50° C. or lower, more preferably 40° C. or lower. After the liquefied crude 4,4'-diaminodiphenylmethane is cooled to a desired temperature, it may be kept standing at the same temperature, if desired.

If necessary, 4,4'-diaminodiphenylmethane may be added as a seed crystal in the crystallization step.

In the crystallization step, a crystallization amount is usually at least 50% by weight, preferably at least 70% by weight, more preferably at least 90% by weight based on the weight of liquefied crude 4,4'-diaminodiphenylmethane. An uncrystallized portion may be removed through the bottom valve of the reactor.

C., 35.7 g, 37.1 g and 30.4 g of the melts Nos. 1, 2 and 3 (103.2 g in total) were removed, respectively to obtain 44.6 g of purified 4,4'-diaminodiphenylmethane [composition: 98.1% of 4,4'-diaminodiphenylmethane; 1.1% of 4,2'-diaminodiphenylmethane; 0.7% of $\alpha,\alpha'$-di(4-aminophenyl)-3,5-xylidine; 0.1% of N-methyl-4,4'-diaminodiphenylmethane].

The above results are summarized in Table 1.

TABLE 1

|  | Melting temp. (°C.) | Melting time | Weight (g) | 4,4'-[3] (%) | 4,2'-[4] (%) | Trinuclear[5] product (%) | N—CH$_3$ compound[6] (%) |
|---|---|---|---|---|---|---|---|
| Charged[1] | — | — | 147.8 | 94.1 | 3.4 | 2.3 | 0.3 |
| Melt No. 1 | 81 → 88 | 3 hrs. | 35.7 | 87.8 | 6.4 | 4.9 | 0.7 |
| Melt No. 2 | 88 → 91 | 30 min. | 37.1 | 93.1 | 3.9 | 2.7 | 0.3 |
| Melt No. 3 | 91 → 92 | 10 min. | 30.4 | 95.9 | 2.3 | 1.6 | 0.2 |
| Purified[2] | — | — | 44.6 | 98.1 | 1.1 | 0.7 | 0.1 |

Note:
[1] Crude 4,4'-diaminodiphenylmethane.
[2] Purified 4,4'-diaminodiphenylmethane.
[3] 4,4'-Diaminodiphenylmethane.
[4] 4,2'-diaminodiphenylmethane.
[5] $\alpha,\alpha'$-Di(4-aminophenyl)xylidine.
[6] N-Methyl-4,4'-diaminodiphenylmethane.

The removed uncrystallized liquid of the liquefied 4,4'-diaminodiphenylmethane may be recycled.

PREFERRED EMBODIMENTS OF THE INVENTION

The purification method of the present invention will be illustrated by following Examples, which will not limit the scope of the present invention in any way.

In the following Examples, "%" is by weight.

The crude 4,4'-diaminodiphenylmethane used in the following Examples was prepared by reacting aniline and formaldehyde and adjusting a composition by distilating the reaction product under reduced pressure.

EXAMPLE 1

(1) In a vessel equipped with a nitrogen inlet tube at its upper part, crude 4,4'-diaminodiphenylmethane [composition: 94.1% of 4,4'-diaminodiphenylmethane; 3.4% of 4,2'-diaminodiphenylmethane; 2.3% of $\alpha,\alpha'$-di(4-aminophenyl)-3,5-xylidine; 0.3% of N-methyl-4,4'-diaminodiphenylmethane] (147.8 g) was charged and heated to 95° C. While adding seed crystals of 4,4'-diaminodiphenylmethane, the liquefied crude 4,4'-diaminodiphenylmethane was cooled down to 60° C. at a cooling rate of 2° C./hour and further to room temperature, and kept standing at room temperature for 12 hours, whereby all the crude 4,4'-diaminodiphenylmethane was crystallized.

(2) The crystal obtained in the above step (1) was heated from 60° to 81° C. at a heating rate of 2° C./hour, from 81° to 88° C. over a period of 3 hours, from 88° to 91° C. over a period of 30 minutes and from 91° to 92° C. over a period of 10 minutes. At 88° C., 91° C. and 92°

EXAMPLE 2

(1) In a vessel equipped with a nitrogen inlet tube at its upper part, crude 4,4'-diaminodiphenylmethane [composition: 98.6% of 4,4'-diaminodiphenylmethane; 1.4% of 4,2'-diaminodiphenylmethane] (144.1 g) was charged and heated to 95° C. While adding seed crystals of 4,4'-diaminodiphenylmethane, the liquefied crude 4,4'-diaminodiphenylmethane was cooled down to 60° C. at a cooling rate of 2° C./hour and further to room temperature, and kept standing at room temperature for 12 hours, whereby all the crude 4,4'-diaminodiphenylmethane was crystallized.

(2) The crystal obtained in the above step (1) was heated from 60° to 81° C. at a heating rate of 2° C./hour, from 81° to 91° C. over a period of 11 hours, from 91° to 92° C. over a period of 1 hour and from 92° to 93° C. over a period of 10 minutes. At 91° C., 92° C. and 93° C., 40.7 g, 33.4 g and 22.8 g of the melts Nos. 1, 2 and 3 (96.9 g in total) were removed, respectively to obtain 47.2 g of purified 4,4'-diaminodiphenylmethane [composition: 99.7% of 4,4'-diaminodiphenylmethane; 0.3% of 4,2'-diaminodiphenylmethane].

The above results are summarized in Table 2.

TABLE 2

|  | Melting temp. (°C.) | Melting time | Weight (g) | 4,4'-[3] (%) | 4,2'-[4] (%) | Trinuclear[5] product (%) | N—CH$_3$ compound[6] (%) |
|---|---|---|---|---|---|---|---|
| Charged[1] | — | — | 144.1 | 98.6 | 1.4 | N.D | N.D |
| Melt No. 1 | 81 → 91 | 11 hrs. | 40.7 | 97.6 | 2.4 | N.D. | N.D. |
| Melt No. 2 | 91 → 92 | 1 hr. | 33.4 | 97.9 | 2.1 | N.D. | N.D. |
| Melt No. 3 | 92 → 93 | 10 min. | 22.8 | 98.9 | 1.1 | N.D. | N.D. |
| Purified[2] | — | — | 47.2 | 99.7 | 0.3 | N.D. | N.D. |

Note:
[1]-[6] See the Note for Table 1.
N.D. Not detected.

EXAMPLE 3

(1) In a vessel equipped with a nitrogen inlet tube at its upper part, crude 4,4'-diaminodiphenylmethane [composition: 90.8% of 4,4'-diaminodiphenylmethane; 7.2% of 4,2'-diaminodiphenylmethane; 1.4% of $\alpha,\alpha'$-di(4-aminophenyl)-3,5-xylidine; 0.7% of N-methyl-4,4'-diaminodiphenylmethane] (151.4 g) was charged and heated to 95° C. While adding seed crystals of 4,4'- diaminodiphenylmethane, the liquefied crude 4,4'-diaminodiphenylmethane was cooled down to 60° C. at a cooling rate of 1° C./hour and further to room temperature, and kept standing at room temperature for 12 hours, whereby all the crude 4,4'-diaminodiphenylmethane was crystallized.

(2) The crystal obtained in the step (1) was heated from 70° to 81° C. over a period of 2 hours, from 81° to 86° C. over a period of 6 hours, from 86° to 89° C. over a period of 2.5 hours, from 89° to 90° C. over a period of 2.5 hours, from 90° to 92° C. over a period of 1.5 hours and kept standing at 92° C. for 30 minutes. At 81° C., 86° C., 89° C., 90° C. and 92° C. (before and after being kept standing), 19.6 g, 21.4 g, 20.5 g, 18.0 g, 20.1 g and 19.5 g of the melts Nos. 1 to 6 (119.1 g in total) were removed, respectively to obtain 32.3 g of purified 4,4'-diaminodiphenylmethane [composition: 98.6% of 4,4'-diaminodiphenylmethane; 0.9% of 4,2'-diaminodiphenylmethane; 0.5% of α,α'-di(4-aminophenyl)-3,5-xylidine; 0.1% of N-methyl-4,4'-diaminodiphenylmethane].

The above results are summarized in Table 3.

TABLE 3

| | Melting temp. (°C.) | Melting time | Weight (g) | 4,4'-*3) (%) | 4,2'-*4) (%) | Trinuclear*5) product (%) | N—CH3 compound*6) (%) |
|---|---|---|---|---|---|---|---|
| Charged*1) | — | — | 151.4 | 90.8 | 7.2 | 1.4 | 0.7 |
| Melt No. 1 | 70 → 81 | 2 hrs. | 19.6 | 75.3 | 20.3 | 2.9 | 1.4 |
| Melt No. 2 | 81 → 86 | 6 hrs. | 21.4 | 83.2 | 13.8 | 2.0 | 1.0 |
| Melt No. 3 | 86 → 89 | 2.5 hrs. | 20.5 | 89.0 | 9.0 | 1.5 | 0.5 |
| Melt No. 4 | 89 → 90 | 2.5 hrs. | 18.0 | 93.4 | 5.2 | 1.0 | 0.4 |
| Melt No. 5 | 90 → 92 | 1.5 hrs. | 20.1 | 96.1 | 2.9 | 0.8 | 0.3 |
| Melt No. 6 | 92° C. | 30 min. | 19.5 | 97.4 | 1.8 | 0.6 | 0.2 |
| Purified*2) | — | — | 32.3 | 98.6 | 0.9 | 0.5 | 0.1 |

Note:
*1)–*6)See the Note for Table 1.

EXAMPLE 4

(1) In a vessel equipped with a nitrogen inlet tube at its upper part, crude 4,4'-diaminodiphenylmethane [composition: 92.0% of 4,4'-diaminodiphenylmethane; 7.3% of 4,2'-diaminodiphenylmethane; 0.2% of α,α'-di(4-aminophenyl)-3,5-xylidiene; 0.6% of N-methyl-4,4'-diaminodiphenylmethane] (142.8 g) was charged and heated to 95° C. While adding seed crystals of 4,4'-diaminodiphenylmethane, the liquefied crude 4,4'-diaminodiphenylmethane was cooled down to 60° C. at a cooling rate of 1° C./hour and further to room temperature, and kept standing at room temperature for 12 hours, whereby all the crude 4,4'-diaminodiphenylmethane was crystallized.

(2) The crystal obtained in the above step (1) was heated from 70° to 87° C. over a period of 16 hours, from 87° to 90° C. over a period of 3.5 hours and from 90° to 91° C. over a period of 2 hours. At 87° C., 90° C. and 91° C., 42.7 g, 20.6 g and 14.8 g of the melts Nos. 1, 2 and 3 (78.1 g in total) were removed, respectively to obtain 64.7 g of purified 4,4'-diaminodiphenylmethane [composition: 98.0% of 4,4'-diaminodiphenylmethane; 1.4% of 4,2'-diaminodiphenylmethane; 0.6% of N-methyl-4,4'-diaminodiphenylmethane]. α,α'-Di(4-aminophenyl)-3,5-xylidine was not detected.

The above results are summarized in Table 4.

TABLE 4

| | Melting temp. (°C.) | Melting time | Weight (g) | 4,4'-*3) (%) | 4,2'-*4) (%) | Trinuclear*5) product (%) | N—CH3 compound*6) (%) |
|---|---|---|---|---|---|---|---|
| Charged*1) | — | — | 142.8 | 92.0 | 7.3 | 0.2 | 0.6 |
| Melt No. 1 | 70 → 87 | 16 hrs. | 42.7 | 80.4 | 17.3 | 0.9 | 1.4 |
| Melt No. 2 | 87 → 90 | 3.5 hrs. | 20.6 | 91.3 | 7.5 | 0.3 | 0.9 |
| Melt No. 3 | 90 → 91 | 2 hrs. | 14.8 | 95.3 | 3.9 | N.D. | 0.8 |
| Purified*2) | — | — | 64.7 | 98.0 | 1.4 | N.D. | 0.6 |

Note:
*1)–*6)See the Note for Table 1.
N.D. Not detected.

What is claimed is:

1. A method for the purification of 4,4'-diaminodiphenylmethane comprising partially melting a crystal of crude 4,4'-diaminodiphenylmethane and removing a melt to obtain high purity 4,4'-diaminodiphenylmethane, wherein said crystal of crude 4,4'-diaminodiphenylmethane is prepared by reacting aniline and formaldehyde.

2. The method for the purification of 4,4'-diaminodiphenylmethane according to claim 1 wherein said crystal of crude 4,4'-diaminodiphenylmethane contains at least 90% by weight of 4,4'-diaminodiphenylmethane.

3. The method for the purification of 4,4'-diaminodiphenylmethane according to claim 1, wherein a temperature for partially melting said crystal of crude 4,4'-diaminodiphenylmethane is in a range between 70° C. and 93° C.

4. The method for the purification of 4,4'-diaminodiphenylmethane according to claim 1, which further comprises liquefying crude 4,4'-diaminodiphenylmethane and crystallizing it by gradual cooling to obtain said crystal of crude 4,4'-diaminodiphenylmethane.

5. The method for the purification of 4,4'-diaminodiphenylmethane according to claim 4, wherein crude 4,4'-diaminodiphenylmethane is liquefied by melting.

6. The method for purification of 4,4'-diaminodiphenylmethane according to claim 1, wherein said crystal of crude 4,4'-diaminodiphenylmethane is heated at a heating rate of 6° C./hour or less.

7. The method for the purification of 4,4'-diaminodiphenylmethane according to claim 1, wherein said crystal of crude 4,4'-diaminodiphenylmethane is heated at a heating rate of 1° C./hour or less.

8. The method for the purification of 4,4'-diaminodiphenylmethane according to claim 1, wherein the amount of the melt is from 20% to 90% by weight based on the weight of the charged crystal of crude 4,4'-diaminodiphenylmethane.

9. The method for purification of 4,4'-diaminodiphenylmethane according to claim 1, wherein the amount of the melt is from 60% to 80% by weight based on the weight of the charged crystal of crude 4,4'-diaminodiphenylmethane.

10. The method for purification of 4,4'-diaminodiphenylmethane according to claim 1, wherein the melt is removed through a bottom valve of a reactor charged with the crude 4,4'-diaminodiphenylmethane.

11. The method for purification of 4,4'-diaminodiphenylmethane according to claim 1, wherein the melt is removed successively.

12. The method for purification of 4,4'-diaminodiphenylmethane according to claim 1, wherein the crystal of crude 4,4'-diaminodiphenylmethane is prepared by (1) liquefying crude 4,4'-diaminodiphenylmethane which has been prepared by reacting aniline and formaldehyde, and (2) crystallizing the reaction product from the step (1) by gradual cooling to 60° C.

13. The method for purification of 4,4'-diaminodiphenylmethane according to claim 1, wherein the reaction product from the step (1) is cooled at a cooling rate of 5° C./hour or less.

* * * * *